US005672157A

United States Patent [19]

Gallagher et al.

[11] Patent Number: 5,672,157

[45] Date of Patent: Sep. 30, 1997

[54] LUMBAR TRACTION APPARATUS

[76] Inventors: Shawn Gallagher, 375 Glendening Rd., Orange Park, Fla. 32073; Timothy Brunelle, 4365 Cedar Rd., Orange Park, Fla. 32065

[21] Appl. No.: 336,515

[22] Filed: Nov. 9, 1994

[51] Int. Cl.$^{6}$ .......... A61F 5/00

[52] U.S. Cl. .......... 602/32; 602/36; 606/241

[58] Field of Search .......... 601/5, 23, 24, 601/35; 602/32–36; 606/241

[56] References Cited

U.S. PATENT DOCUMENTS

| | | | |
|---|---|---|---|
| 4,356,816 | 11/1982 | Granberg . | |
| 4,466,427 | 8/1984 | Granberg . | |
| 4,494,533 | 1/1985 | Sgroi et al. . | |
| 4,602,619 | 7/1986 | Wolf et al. . | |
| 4,608,969 | 9/1986 | Hamlin . | |
| 4,664,101 | 5/1987 | Granberg . | |
| 4,995,378 | 2/1991 | Dyer et al. . | |
| 5,512,040 | 4/1996 | Mathews | 602/36 |

FOREIGN PATENT DOCUMENTS

| | | | |
|---|---|---|---|
| 92349 | 9/1968 | France | 602/36 |

*Primary Examiner*—Richard J. Apley
*Assistant Examiner*—Jeanne M. Clark
*Attorney, Agent, or Firm*—Frank L. Kubler

[57] ABSTRACT

A lumbar traction apparatus for applying traction to the back of a patient includes a frame structure, a winch support structure extending above the frame structure, a winch assembly having a hand crank mounted on the winch support structure, two harnesses for wrapping around the torso of the patient, tensioning cords extending from the winch assembly each to one of the two harnesses, so that rotating the hand crank on the winch assembly gathers both of these cords and thereby pulls the harnesses apart to create traction in the back of the patient. The frame structure preferably includes a connecting segment, a first arm segment substantially perpendicular and joined to the connecting segment, and a second arm segment substantially perpendicular and joined to the connecting segment and spaced apart from the first arm segment. The connecting segment is preferably formed of two telescoping portions for convenient assembly and disassembly of the frame structure for transport and storage. The winch support structure is preferably located substantially at the middle of the connecting segment and above the patient.

20 Claims, 8 Drawing Sheets

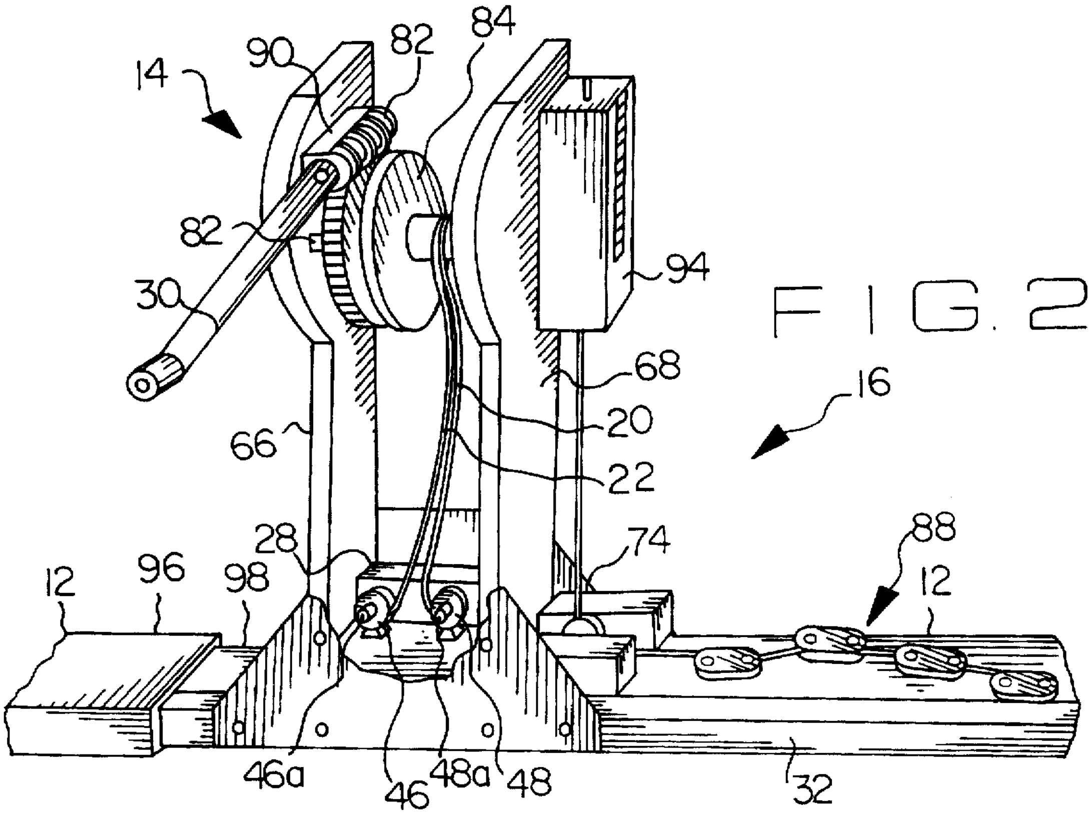
FIG. 2
FIG. 5
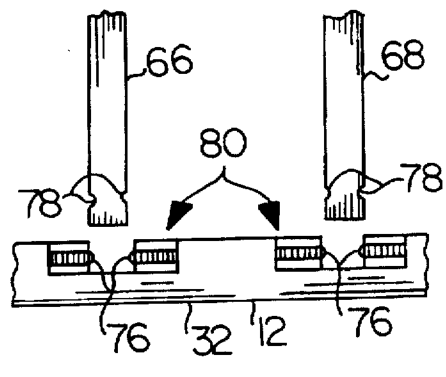
FIG. 8
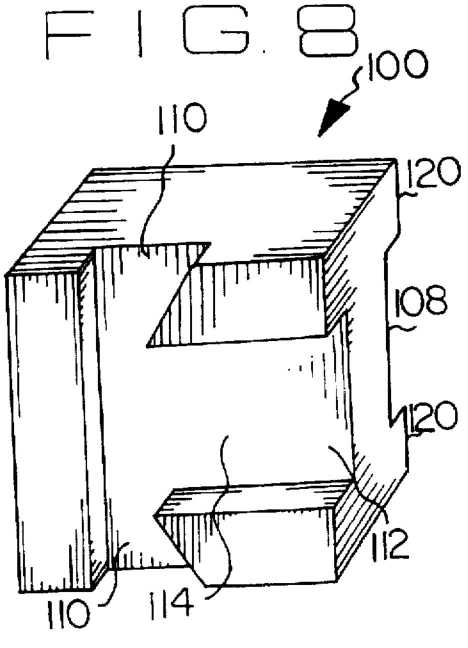

LUMBAR TRACTION APPARATUS

BACKGROUND OF THE INVENTION

1. Field of the Invention

The present invention relates generally to the field of devices for applying traction to the spine of a patient. More specifically, it relates to a lumbar traction apparatus including a horizontal frame structure having an open side through which a patient enters the frame structure, a winch assembly mounted on a detachable post extending vertically from the frame structure, tensioning cords extending from the winch assembly down the post to pulleys at the base of the post, along the frame structure and behind the head and waist of the patient to a pair of harnesses wrapped around the torso of the patient. Rotating a crank on the winch assembly gathers the cords leading to both harnesses to pull the harnesses away from each other and thereby create traction in the patient's lumbar area. The frame structure is preferably C-shaped, having a connecting segment for extending beside the patient, and first and second arm segments perpendicular to and extending from opposing connecting segments.

2. Description of the Prior Art

There have long been devices for creating lumbar traction in patients.

Granberg, U.S. Pat. No. 4,664,101, issued on May 12, 1987, and U.S. Pat. No. 4,466,427, issued on Aug. 21, 1984, disclose related versions of a cervical and lumbar traction apparatus. Granberg includes a horizontal, rectangular frame in which the patient reclines, which is centrally hinged to fold in half for storage. The later Granberg includes a leg supporting platform attached to one end of the frame. A hydraulic cylinder and piston assembly is mounted to one side of the frame and has a pumping handle. A traction cord extends from the assembly along frame members to the foot of the frame, and then underneath the patient's waist to a pelvic belt. An anchoring belt secured to the frame with bolts to hold the patient in place while the pelvic belt is pulled toward the foot of the frame. A problem with Granberg is that the patient always experiences the inconvenience of having to cross over a frame member to enter the frame and use the apparatus. Another problem with Granberg is that tension in the traction cord would create instability and the possibility of buckling at the frame hinges. Another problem is that the traction apparatus only applies tension to one belt while the other belt remains fixed. As a result, the apparatus may tend to slide relative to the patient while slack is gathered, and if on a table may fall off and injure the patient. Another problem with Granberg is that the hydraulic cylinder and piston assembly is slow to gather slack, and does not give the patient a direct feel of the tension being applied. Furthermore, the range of traction magnitudes attainable with the mass produced and marketed cylinder and piston assembly would be narrow. Yet providing a long cylinder assembly would be prohibitively expensive. For comfortable traction one needs plenty of slack in the traction cords so that the belts may be placed in a position where they slide until they grip the patient securely. The limited travel possible with the Granberg cylinder and piston assembly requires that the belts be positioned fairly precisely and skillfully. The pumping action is also ergonomically inefficient. Less than half of the pumping motion of the patient delivers force to tighten the cord. A winch assembly replacing the Granberg cylinder and piston assembly would solve this efficiency problem, but the position of the assembly on Granberg directly beside the patient would make the rotational motion awkward for the patient to deliver. In addition, Granberg does not provide the recommended right angle leg positioning for lumbar traction, as can be seen in the Granberg Figures. Finally, Granberg is structurally complex with many parts and confusing to assemble, heavy, aesthetically unappealing, and presents the hazards of exposed mechanical parts.

Granberg, U.S. Pat. No. 4,356,816, issued on Nov. 2, 1982, teaches a traction apparatus similar to the above-described Granberg devices. This Granberg device includes a heavy, rectangular frame bed with a cushion on top. Rather than providing a hydraulic cylinder and piston assembly to tighten the traction cord, a lever and ratchet assembly are substituted. This Granberg apparatus presents all the disadvantages and problems identified above for the later versions, except that the frame does not fold and so is potentially sturdier. Yet the frame does not break down into a compact size, and so is awkward and cumbersome. The back and forth ratchet action is just as ergonomically inefficient as the lever-operated hydraulic assembly.

Hamlin, U.S. Pat. No. 4,608,969, issued on Sep. 2, 1986, reveals a portable traction apparatus. Two spaced apart supports have guide rails therebetween along which a foot carriage travels. A flat body-supporting panel mounts removably over the base. The feet of the patient are strapped into the foot carriage, and a manually operated, hydraulic pump or jack urge the foot carriage toward a forward position on the rails. A problem with Hamlin is that the strapping of the feet to the carriage prevents the patient from achieving the safe and recommended double right angle bend in the legs during traction. Another problem is that this method of traction applies a force to every joint in between the points of attachment. There is a good possibility that at least one of these joints would not tolerate the necessary tension. Other problems are that the hydraulic cylinder or jack action of Hamlin prevents the patient from having a direct feel for the tension being applied, is slow to gather slack and is ergonomically inefficient.

Wolf, et al., U.S. Pat. No. 4,602,619, issued on Jul. 29, 1986, discloses a spinal traction method and apparatus. Wolf et al. includes a rectangular frame with several inner cross members supporting a back supporting wedge. A head post extends vertically from an end of the frame for supporting a neck harness. An elevated leg supporting platform is attached to the end of the frame opposite the head post. A crane structure and waist harness project over and above the frame, are attached to the leg supporting platform, and are powered by a motorized drive screw. A problem with Wolf et al. is that, apart from traction supplied by the neck harness, only traction perpendicular to the spine is provided. Another problem is that the frame, leg supporting platform and crane structure together constitute a very expensive and complicated apparatus. Still another problem is that the motorized crane structure does not provide the patient with a direct feel for the amount of traction being applied.

Dyer et al., U.S. Pat. No. 4,995,378, issued on Feb. 26, 1991, teaches a therapeutic table for providing traction to the lumbar area of a patient. Dyer et al. includes a frame, a table top having an upper-body section fixed with respect to the frame, a lower-body section slidable with respect to the frame, grips to anchor the upper body to the upper body section and a pelvic belt for anchoring the lower body to the lower body section. A cylinder and piston drive assembly slides the lower body section along the frame in increasing and decreasing cycles to apply traction to the lumbar area. A problem with Dyer et al. is that it would be prohibitively expensive. Another problem is that the patient cannot take the recommended bent leg position during traction. Still another problem is that the cylinder and piston arrangement once again prevents the patient from having the direct feel of how much tension is being applied. Another problem with Dyer et al. is that hanging onto the hand grips would be extremely tiring.

Sgroi, et al., U.S. Pat. No. 4,494,533, issued on Jan. 22, 1985, reveals a traction device from which a patient can do pull-up and inverted sit-up exercises. A complex, expensive and bulky frame structure supports the patient during these exercises. Sgroi et al. is not only cumbersome, costly and awkward to use, but fails to provide the variations in traction magnitude desirable for most treatment programs.

It is thus an object of the present invention to provide a lumbar traction apparatus with an open frame structure which permits the patient to enter the apparatus without having to cross over a frame member.

It is another object of the present invention to provide such an apparatus which gives the patient direct manual control over the magnitude of applied lumbar tension, rapidly takes up tensioning cord slack, and is quiet to operate.

It is another object of the present invention to provide such an apparatus which provides a wider range of lumbar tension than is available with a standard piston and cylinder tensioning assembly.

It is still another object of the present invention to provide such an apparatus which actively pulls on the lumbar region in opposing directions at once, rather than in only one direction, so that the apparatus undergoes minimal movement relative to the patient during gathering of slack tensioning cord.

It is still another object of the present invention to provide such an apparatus which provides a cord tensioning control in an easy to reach and operate location above the patient.

It is still another object of the present invention to provide such an apparatus which distributes loading so that only a relatively light weight frame structure is needed, such as by subjecting structural members to balanced loading and loading in compression rather than loading in bending.

It is finally an object of the present invention to provide such an apparatus which is relatively inexpensive to manufacture and can be partially disassembled for storage and transport, preferably without need of tools, and which is held together at least in part by tension in the tensioning cords.

SUMMARY OF THE INVENTION

The present invention accomplishes the above-stated objectives, as well as others, as may be determined by a fair reading and interpretation of the entire specification.

A lumbar traction apparatus is provided for applying traction to the back of a patient, including a frame structure, a winch support structure extending above the frame structure, a winch assembly having a hand crank mounted on the winch support structure, two harnesses for wrapping around the torso of the patient, tensioning cords extending from the winch assembly each to one of the two harnesses, so that rotating the hand crank on the winch assembly gathers both of these cords and thereby pulls the harnesses apart to create traction in the back of the patient. The frame structure preferably includes a connecting segment, a first arm segment substantially perpendicular and joined to the connecting segment, and a second arm segment substantially perpendicular and joined to the connecting segment and spaced apart from the first arm segment. The connecting segment is preferably formed of two telescoping portions for convenient assembly and disassembly of the frame structure for transport and storage. The winch support structure is preferably located substantially at the middle of the connecting segment. The winch support structure preferably has a base, and additionally includes first guide pulleys attached to the connecting segment at the base of the winch support structure, second guide pulleys attached to the ends of the connecting segment, and third guide pulleys secured to the arm segments, where the tensioning cords extend from the winch assembly to the first guide pulleys, then the cords extend in opposite directions along the connecting segment to the second guide pulleys, and the cords extend from the second guide pulleys along the arm segments to the third guide pulleys, and each connect to one of the harnesses. The winch support structure preferably includes a pair of spaced apart and substantially vertical members each removably joined to the connecting segment. The vertical members are preferably removably joined to the connecting segment with anchoring plates and fasteners passing through the anchoring plates into the vertical members and into the connecting segment. The winch assembly preferably includes a spool rotatably mounted between the vertical members on an axle bolt, a worm wheel gear attached to the spool to rotate together with the spool and engaged by a worm gear rotatably mounted to the vertical member. A tension measuring scale assembly is optionally provided. A patient leg support box is preferably provided for supporting the lower legs of the patient to place the patient in a safe and effective traction receiving position. The box preferably includes a top wall and a bottom wall and at least one side wall, and where the box additionally includes a channel in the bottom wall for fitting over and around the second arm segment of the frame structure. The box may also include leg retaining projections extending upward from the box top wall. The connecting segment alternatively is formed of a tubular center portion and two telescoping portions which fit into opposing ends of the center portion for convenient assembly and disassembly of the frame structure for transport and storage.

The lower legs of a patient are alternatively supported by a leg support stand to place said patient in a safe and effective traction receiving position, including a top panel having opposing side edges and a front edge and a notch in the front edge sized to receive and retain the legs of the patient, an elongate top panel support member secured across the top panel and extending outward from the opposing side edges of the top panel and having a mounting opening at each end, and two upright assemblies, each upright assembly having a series of mounting ports through one of which a fastener is inserted, the fastener also being inserted into one of the mounting openings. The top panel preferably has a bottom surface and the support member is preferably secured to the bottom surface of the top panel with strap elements fastened to the bottom surface. The upright assemblies preferably are each in the form of a substantially T-shaped panel having stand support leg portions protruding from the horizontal ends of the T-shape, and having a perpendicular slat protruding longitudinally from the vertical portion of the T-shape The upright assemblies may each also include first interconnecting slots on either side of the base of the T-shape to receive the cross braces. The cross braces preferably include second interconnecting slots which interlock with the first interconnecting slots.

The apparatus optionally includes a cervical traction assembly secured to one of the arm members. The cervical traction assembly preferably includes a head halter, a halter post secured to the one arm member, where the cord extends around a first cervical pulley at the base of halter post and around a second cervical pulley at the top of the halter post, and then is clipped to the halter.

BRIEF DESCRIPTION OF THE DRAWINGS

Various other objects, advantages, and features of the invention will become apparent to those skilled in the art from the following discussion taken in conjunction with the following drawings, in which:

FIG. 2 is a perspective close-up view of the winch assembly and of the scale assembly, also showing the telescoping sizing and slide-in interconnection of the two portions of the connecting segment of the frame structure.

FIG. 5 is a front view of the vertical members of the winch supporting post with an example of the snap fastener option.

FIG. 8 is a perspective bottom view of the leg supporting box alone, showing the configuration of the channels for receiving the second arm segment of the frame structure and one of the tensioning cords.

DETAILED DESCRIPTION OF THE PREFERRED EMBODIMENTS

Figure 1:
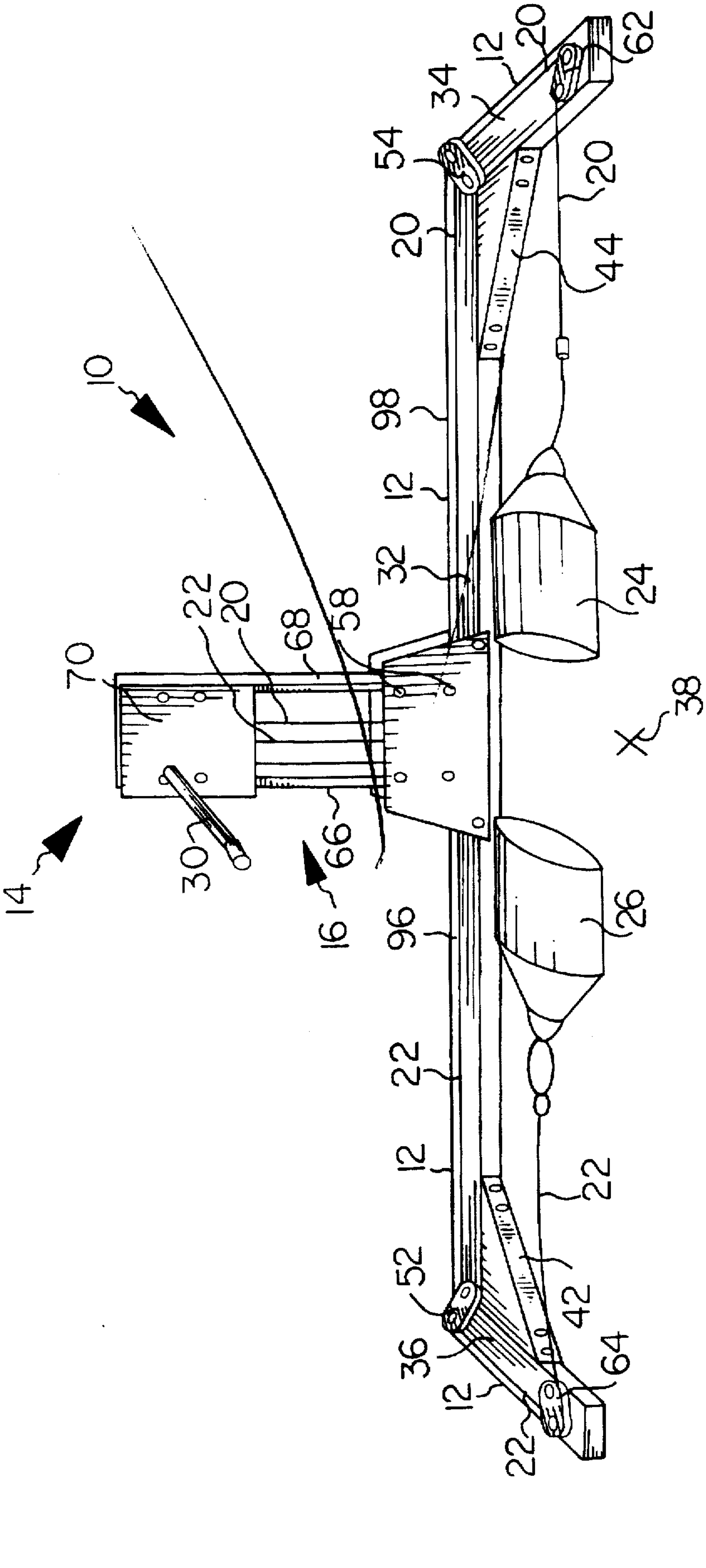
FIG. 1 is a perspective view of the inventive traction apparatus.
Figure 3:
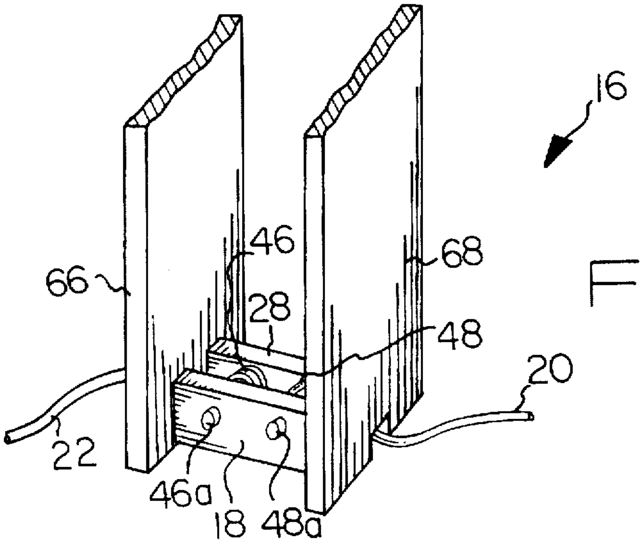
FIG. 3 is a broken away perspective view of the removable post, with the mounting plates removed, revealing the post base members and the mounting between these members of the two first guide pulleys.
Figure 4:
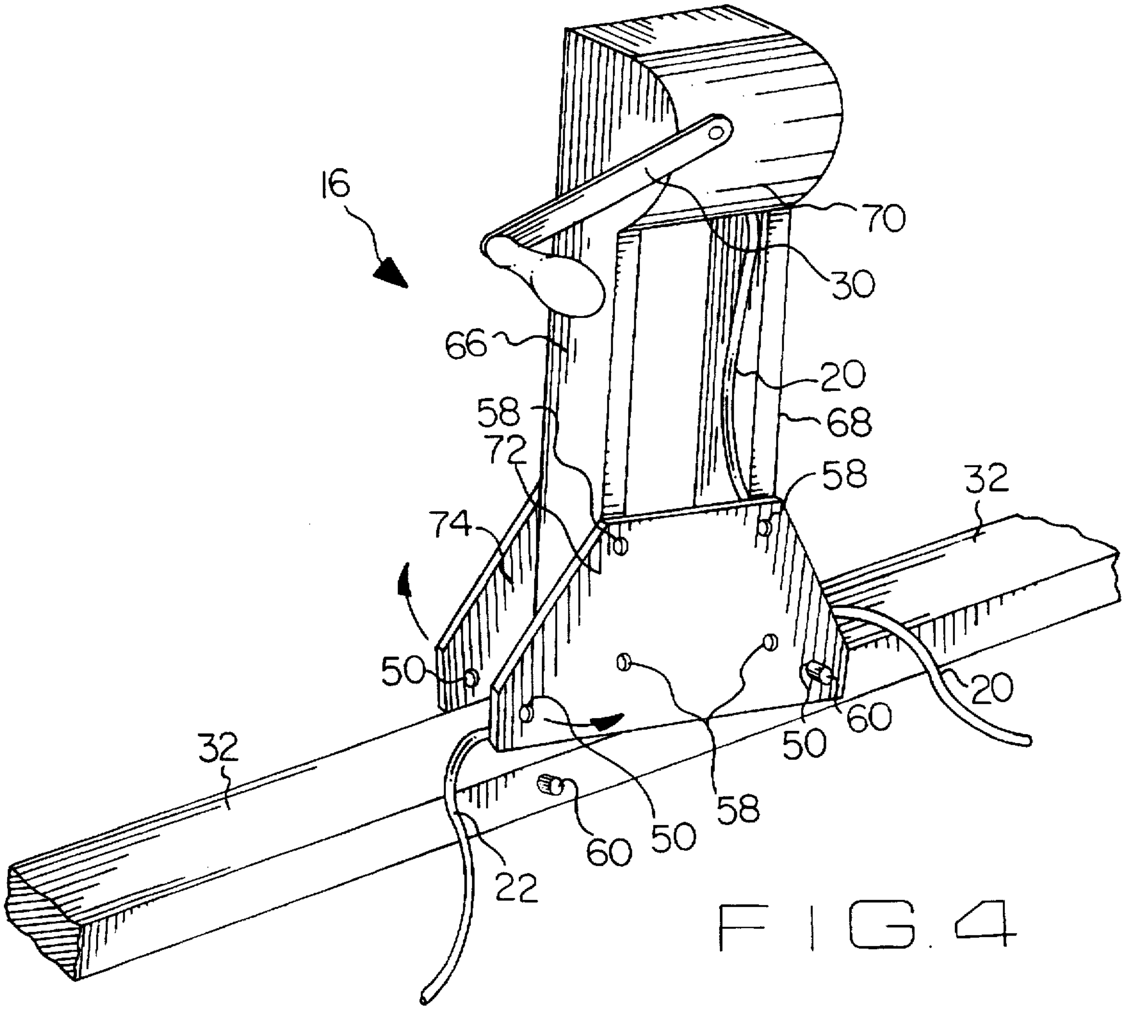
FIG. 4 is a perspective close-up view of one version of the removable post having the resiliently spreadable mounting plates with ports fitting over connecting segment side studs.
Figure 6:
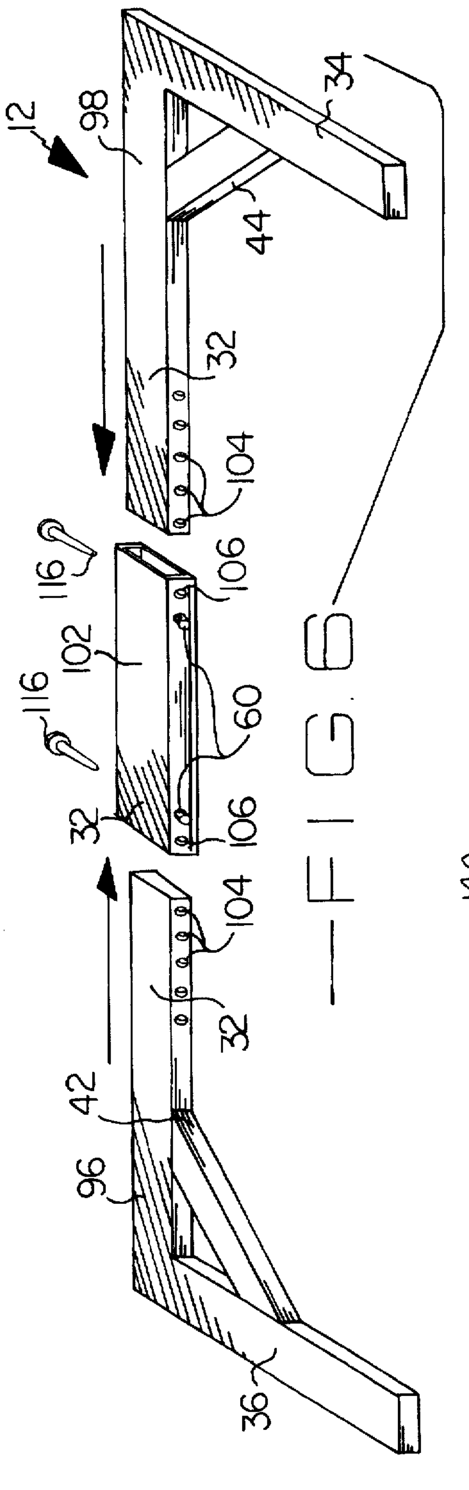
FIG. 6 is a disassembled, perspective view of the version of the frame having a center portion into which the telescoping portions adjustably fit.
Figure 7:
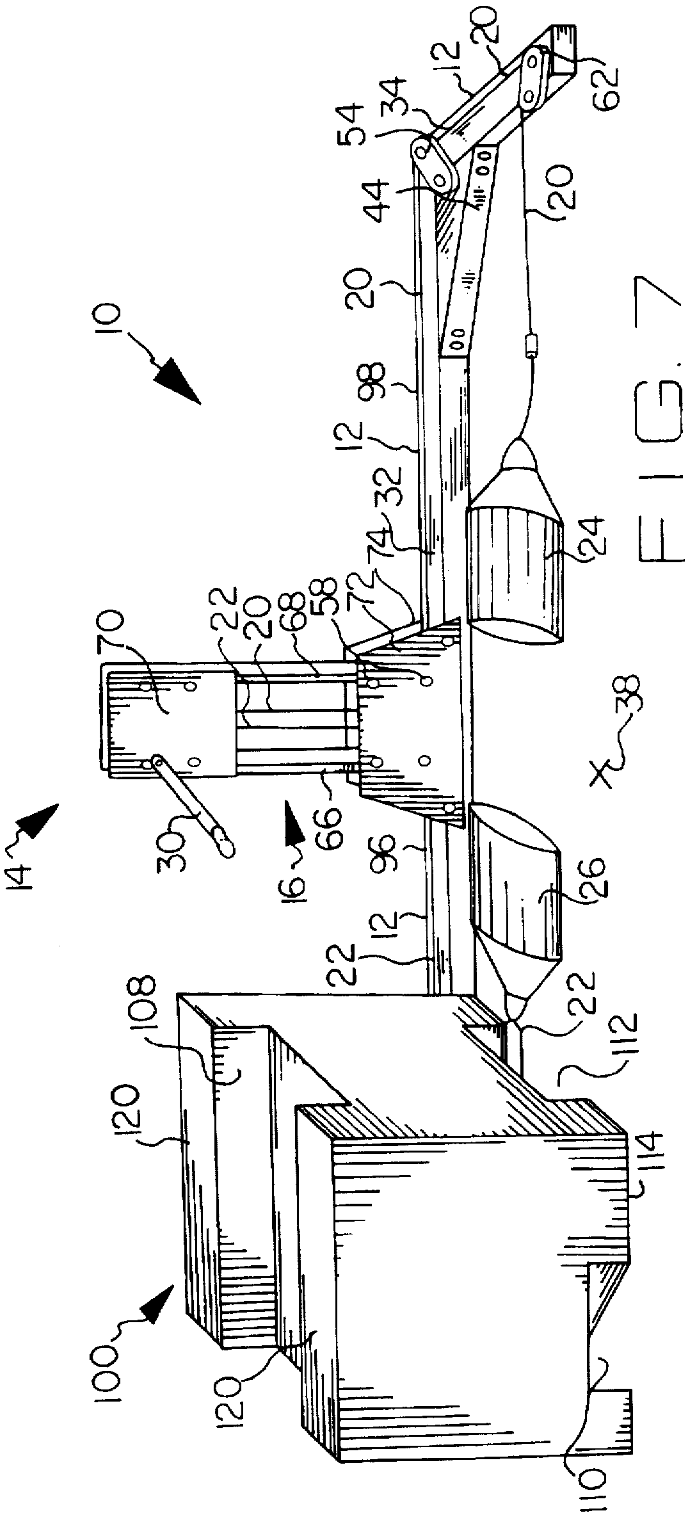
FIG. 7 is a perspective view as in FIG. 1, with the inventive leg supporting box in place for use.
Figure 9:
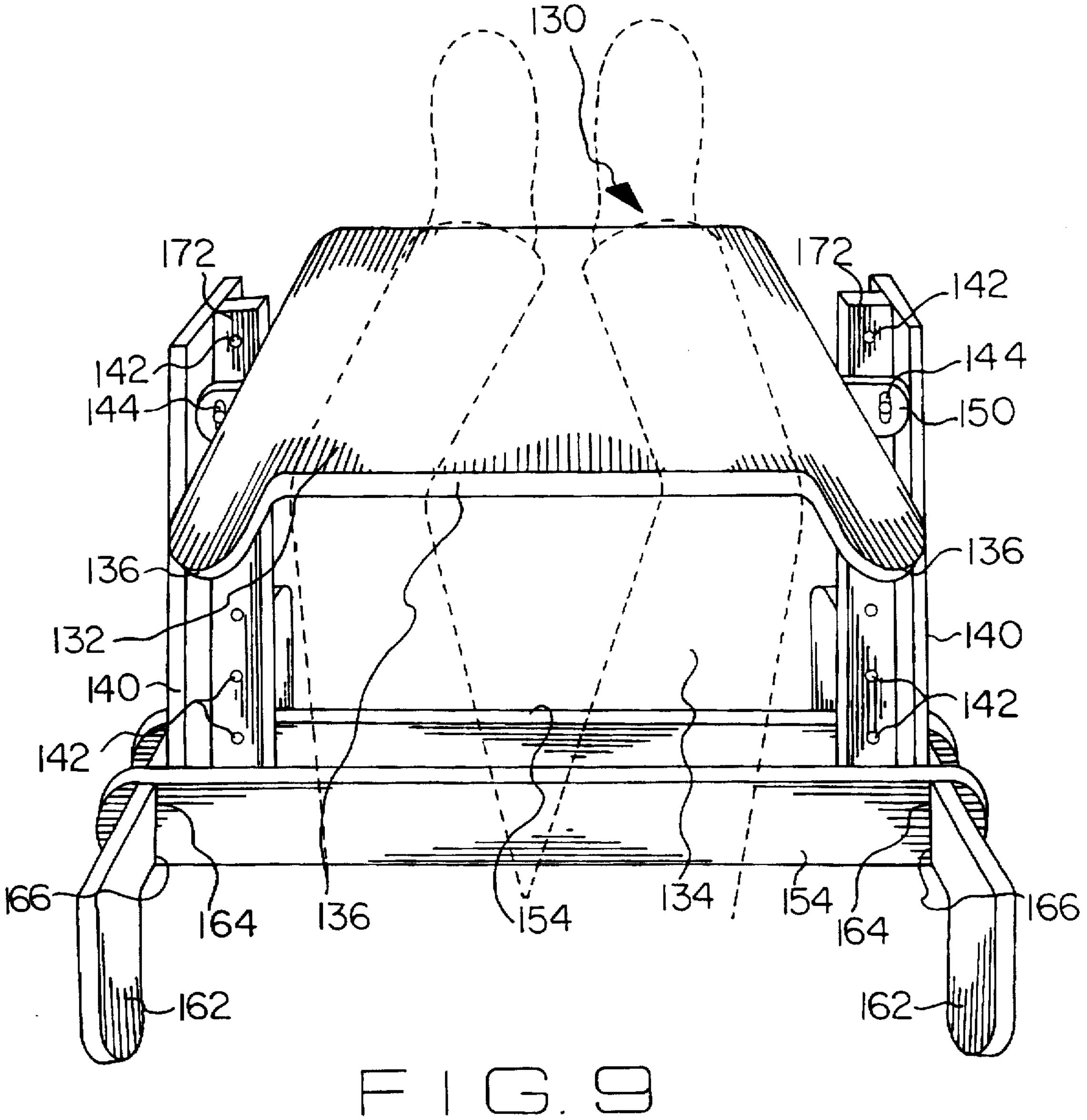
FIG. 9 is perspective view of the inventive leg support stand assembled for use. The position of a patient using the stand is indicated in broken lines.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Referring to FIGS. 1–12, a lumbar traction apparatus 10 is disclosed for applying therapeutic tension to the lumbar area of a patient. Apparatus 10 includes a horizontal frame structure 12, a winch assembly 14 mounted on a detachable post 16 extending vertically upward from frame structure 12, tensioning cords 20 and 22 extending from winch assembly 14 down post 16, along frame structure 12 and behind the head and lower back of the patient. Cords 20 and 22 connect to one of harnesses 24 and 26, respectively, which are wrapped around the torso of the patient at opposing ends of the lumbar area. Rotating a crank 30 on winch assembly 14 gathers cords 20 and 22 to simultaneously pull harnesses 24 and 26 apart and create traction in the patient's lumbar area. A rotationally balanced solid wheel (not shown) having a circumferential outer edge for hand gripping, or a spoked circular handle grip such as a steering wheel, (not shown) may be substituted for crank 30, for increased ease in hand gripping and turning.

Frame structure 12 preferably has a blocked C-shape and preferably includes a connecting segment 32, a first arm segment 34 perpendicular to and extending from a first end of connecting segment 32, and a second arm segment 36 also perpendicular to and extending from a second end of connecting segment 32. Cross members 42 and 44 add strength. A patient enters frame structure 12 through the open side 38 of the C-shape and lies down beside and substantially parallel with connecting segment 32, with first arm segment 34 extending adjacent to the top of the patient's head. Tensioning cords 20 and 22 extend down post 16 to first guide pulleys 46 and 48 within the base of post 16. Then cords 20 and 22 extend in opposite directions along connecting segment 32 to second guide pulleys 52 and 54 at the ends of segment 32. Cords 20 and 22 extend from pulleys 52 and 54 along arm segments 34 and 36, respectively, to third guide pulleys 62 and 64 at the free ends of segments 34 and 36. From pulleys 62 and 64 cords 20 and 22 extend toward each other and connect to harnesses 24 and 26.

Post 16 is preferably a pair of spaced apart, vertical members 66 and 68 each removably fastened with screws or bolts 58 between a pair of spaced apart mounting plates 72 and 74. See FIG. 2. Plates 72 and 74 are preferably made of a durable, resilient plastic. Pulleys 46 and 48 are rotatably mounted on substantially parallel axles 46a and 48a extending into post base supports 18 and 28. See FIG. 3. Base supports 18 and 28 are in turn fastened to vertical members 66 and 68. Post 16 is preferably removable so that a more compact apparatus 10 configuration may be achieved for transport and storage and to permit one hundred eighty degree rotation of post 16. This rotation orients crank 30 to be alternately accessible to either the patient or to a health care worker.

Two alternative structures are contemplated for making post 16 readily removable. Mounting studs 60 preferably protrude from the side surfaces of connecting segment 32. See FIG. 4. To mount post 16, plates 72 and 74 are spread or bowed apart by hand against the resilience of plates 72 and 74. Plate ports 50 are fitted over and around studs 60. Then plates 72 and 74 are released to spring flat against connecting segment 32. To remove post 16, plates 72 and 74 are again bowed outward by hand so that ports 50 slide off studs 60. Conventional snap engagement fasteners 80 may alternatively be used to mount post 16, as shown in FIG. 5, because very little holding power is required. Spring-loaded knobs 76 may snap into recesses 78 in vertical members 66 and 68.

When apparatus 10 is in use, cords 20 and 22 both pull post 16 down against connecting segment 32 with balanced, stable tension. This use of tension in cords 20 and 22 to strengthen the apparatus framework is an inventive aspect of apparatus 10. Winch assembly 14 preferably includes a cord gathering spool 76 rotatably mounted between members 66 and 68 on an axle bolt 82. A worm wheel 84 is attached to spool 76 to rotate together with spool 76 and is engaged by a worm gear 86 attached to member 66. Worm gear 86 is rotatably mounted on a bracket 90 fastened to member 66, and worm gear 86 extends axially outward to connect to a hand crank 92. A cover housing 70 preferably shields the patient from the moving parts of winch assembly 14. A tension measuring scale assembly 94 is preferably secured to either a side of member 66 or of member 68. See FIG. 2. A series of pulleys 88 may divide the magnitude of tensile loading on cords 20 and 22 into a measurable range for scale assembly 94. Pulleys 88 are preferably secured to an inwardly directed surface of member 66 or 68.

Connecting segment 32 is preferably formed of two telescoping portions 96 and 98 which simply slide together, until portion 96 abuts a stop element (not shown) inside portion 98, to form the C-shaped frame structure 12 when apparatus 10 is to be used. See FIG. 2. Alternatively, telescoping portions 96 and 98 fit into opposite ends of tubular center portion 102. See FIG. 6. A series of adjustment ports 104 are provided in portions 96 and 98, and ports 106 are provided in center portion 102. Portions 96 and 98, and center portion 102 are removably connected with two adjustment pins 116, fitted through registering ports 104 and 106, so that a variety of connecting segment 32 lengths may be attained to correspond with and closely adapt to various heights of users. Portions 96 and 98 are also held together or within center portion 102 by the tension in cords 20 and 22 acting on second guide pulleys 52 and 54. Then, when disassembly is desired, telescoping portions 96 and 98 are simply pulled apart, or out of center portion 102. No tools are needed. And when resilient plates 72 and 74 or snap fasteners are used to connect post 16 to member 32, no tools are needed at all for normal disassembly and assembly of apparatus 10.

A patient leg support box 100 is preferably provided. The patient rests his or her lower legs on the top wall 108 of box 100 to achieve a safer and more effective traction receiving position. See FIG. 7. This position is known as the 90/90 position, because the patient upper legs are directed at a right angle with respect to the patient torso, and the patient lower legs are directed at a right angle with respect to the patient upper legs. Intersecting channels 110 and 112 are preferably provided in the bottom wall 114 of box 100 for fitting over and around frame structure second arm segment 36 and cord 20. See FIG. 8. Leg retaining rails or protrusions 120 are preferably provided at opposing edges of top wall 108 to comfortably hold patient legs in place on top of box 100.

A leg support stand 130 is provided as an alternative to box 100. See FIGS. 9–11. Stand 130 has a plywood top panel 132 with a recess or wide notch 134 cut along a forward edge 136 to receive and retain user legs. See FIG. 9. Top panel 132 is supported by two upright assemblies 140 having several level pairs of top panel mounting ports 142. The elevation of top panel 132 is adjustable by removing wing nuts 144 from bolts 146 extending through mounting ports 142 and through mounting openings 152 in a panel support member 150. Then top panel 132 is moved vertically, either upward or downward, so that mounting openings 152 are located opposite another level pair of mounting ports 142. Bolts 146 are then once again inserted through ports 142 and openings 152, and wing nuts 144 are refastened to bolts 146.

Figure 10:
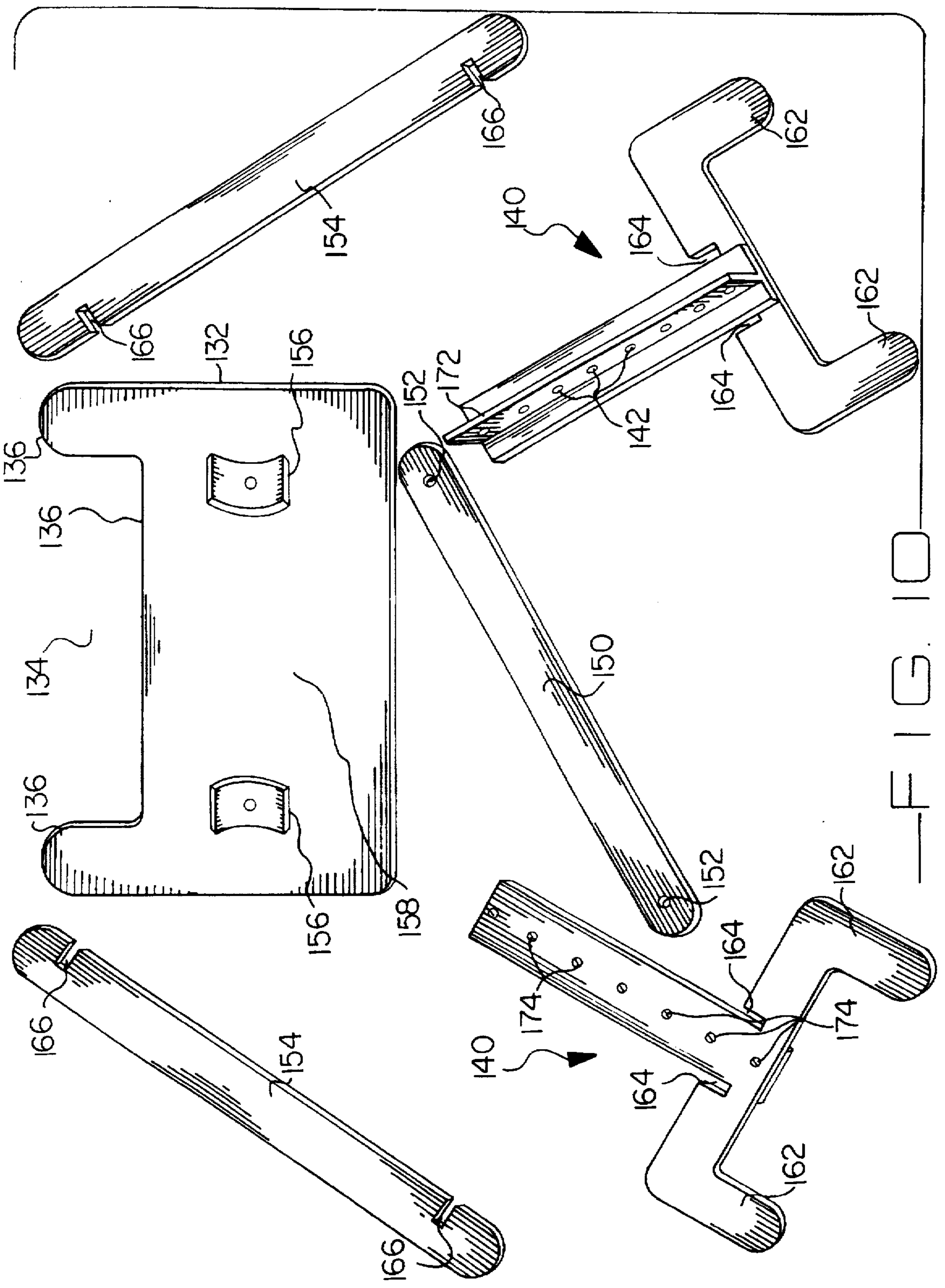
FIG. 10 is a view of the various elements of the leg support stand of FIG. 9 in a disassembled condition.
Figure 11:
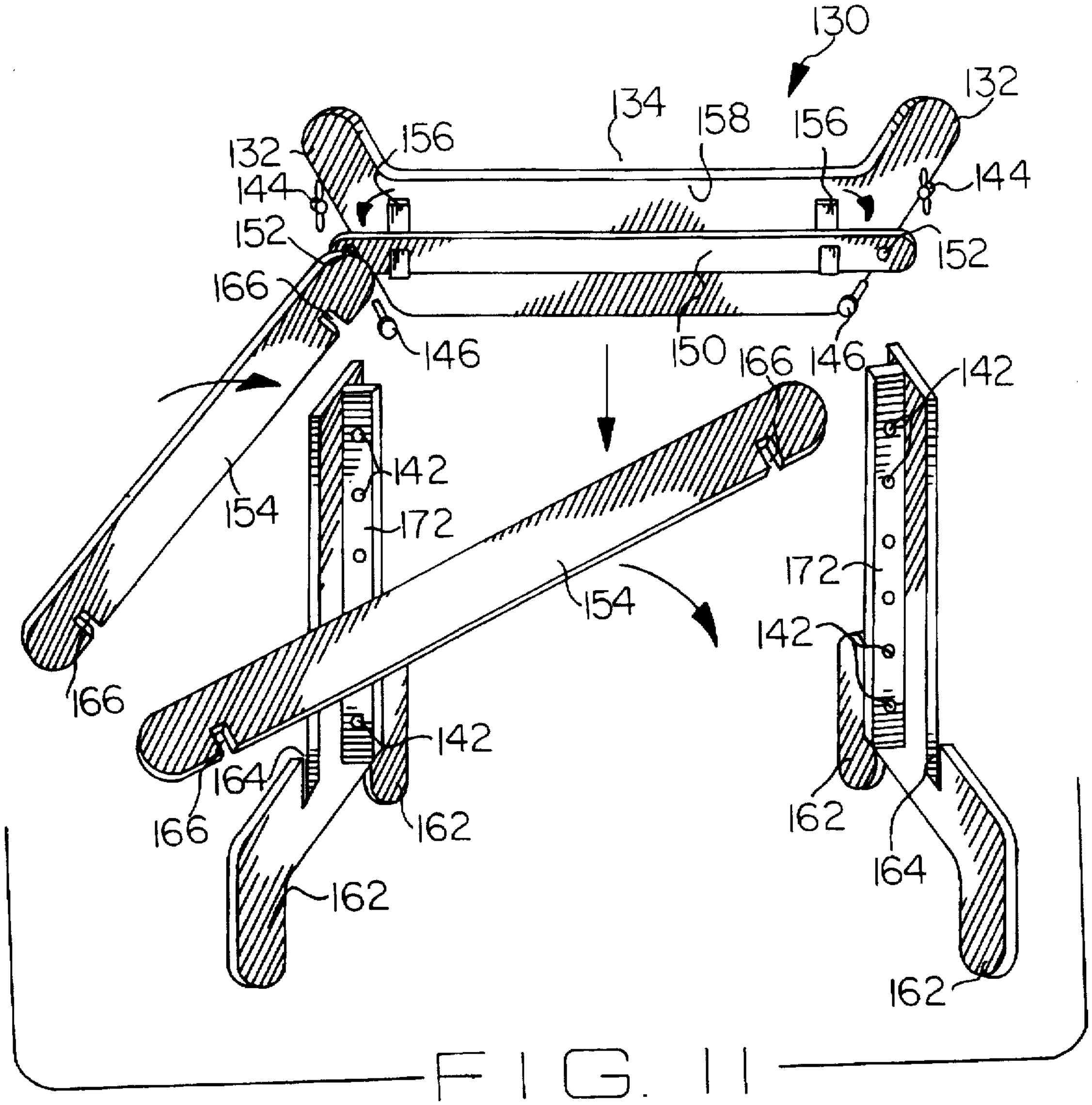
FIG. 11 is a perspective view of the leg support stand of FIG. 9 in the process of being assembled from the elements shown in FIG. 10.

Stand 130 is constructed of several elements shown separated in FIG. 10. These elements include top panel 132, upright assemblies 140, support member 150, and cross braces 154. Stiff, resilient, securing straps 156 are fastened to the lower surface 158 of top panel 132 for snapping around and securing support member 150. Straps 156 may be made of PVC pipe sections. Support member 150 may be a length of PVC tube. Upright assemblies 140 may be T-shaped forms cut from a plywood sheet, with ear portions 162 protruding from the ends of the horizontal segment of the T-shape to act as stand 130 support legs. First interconnecting slots 164 are provided on either side of the vertical segment of the T-shape to receive cross braces 154. Second interconnecting slots 166 are provided in cross braces 154. Upright assemblies 140 and cross braces 154 fit together at slots 164 and 166. See FIG. 11. A perpendicular slat 172 protrudes from the base of the T-shape and has the series of mounting ports 142 along its length. A perpendicular slat 172 is joined to each upright assembly 140 by a series of wood screws 174. Stand 130 is positioned relative to frame structure 12 in the same location and orientation as box 100 is positioned.

Figure 12:
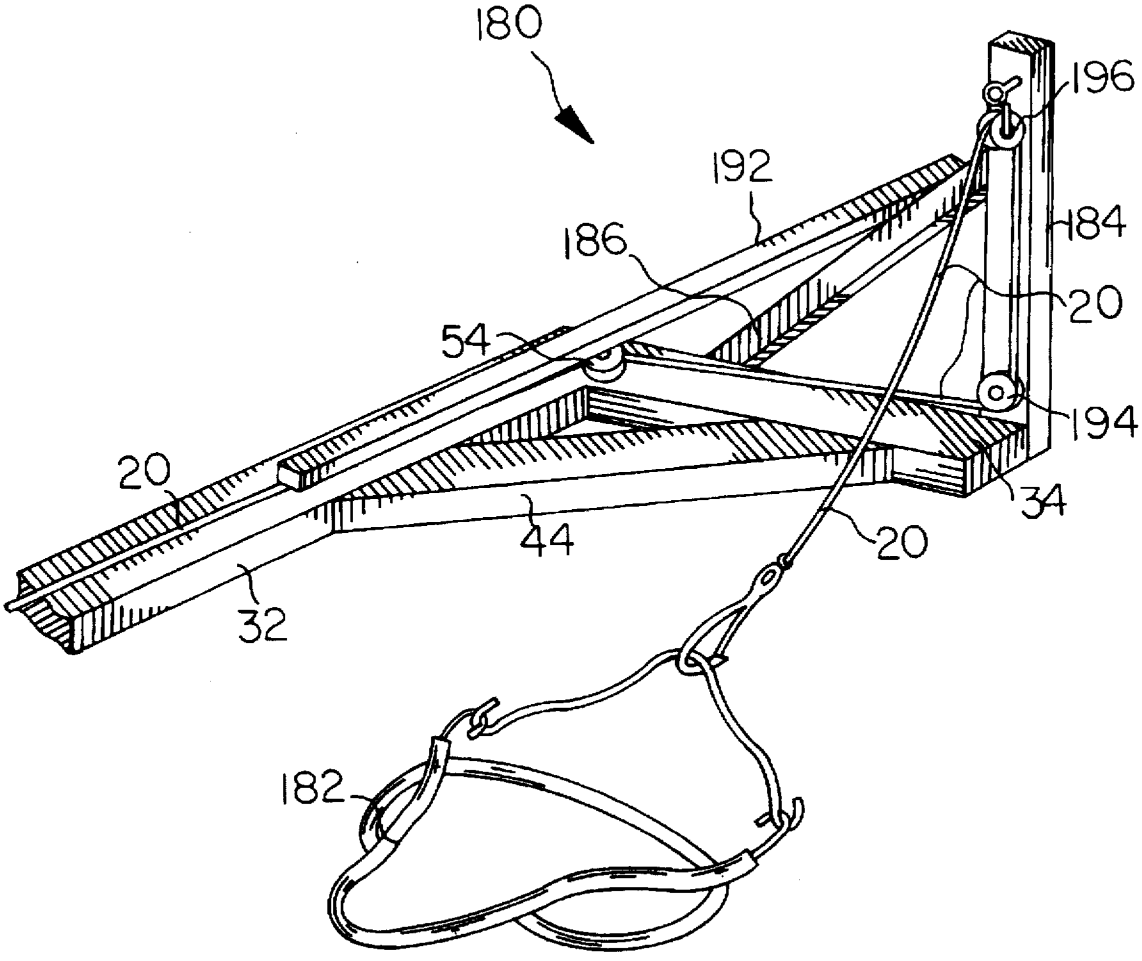
FIG. 12 is perspective view of the inventive cervical traction assembly attached to the apparatus and ready for use.

A cervical traction assembly 180 is optionally provided as shown in FIG. 12. Traction assembly 180 includes a conventional head halter 182, a halter post 184, a first support brace 186 diagonally secured between halter post 184 and first arm segment 34, and a second support brace 192 secured between halter post 184 and connecting portion 32. Cord 20 extends around a first cervical pulley 194 at the base of halter post 184 and around a second cervical pulley 196 at the top of halter post 184. Then cord 20 is clipped to halter 182. Halter post 184, and first and second support braces 186 and 192 are secured with conventional fastening means, such as lag screws (not shown).

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim as my invention:

1. A lumbar traction apparatus for applying traction to the back of a patient, comprising:

a frame structure, a winch support structure extending above said frame structure, a winch assembly having hand crank means mounted on said winch support structure, two harnesses with means for wrapping around the torso of the patient, tensioning cords extending in substantially opposite lateral directions from said winch assembly each to one of said two harnesses, and means for directing said cords in a vertical direction within said winch support structure wherein tension in said cords creates a downward vertical force on said winch assembly and said winch support structure thereby anchoring and stabilizing said winch assembly and said winch support structure on said frame structure, such that rotating said hand crank means on said winch assembly simultaneously gathers both said cords and thereby pulls said harnesses apart, to create traction in the back of the patient, and to substantially balance lateral forces acting on said winch such that said winch is subjected to substantially zero resultant lateral loading.

2. The apparatus of claim 1, additionally comprising tension measuring scale means connected to at least one of said tensioning cords and to said winch support structure.

3. A lumbar traction apparatus for applying traction to the back of a patient, comprising:

a frame structure, a winch support structure extending above said frame structure, a winch assembly having hand crank means mounted on said winch support structure, two harnesses with means for wrapping around the torso of the patient, tensioning cords extending from said winch assembly each to one of said two harnesses, such that rotating said hand crank means on said winch assembly gathers both said cords and thereby pulls said harnesses apart to create traction in the back of the patient, wherein said frame structure comprises a connecting segment, a cantilever first arm segment having a first arm segment free end and having a first arm segment connected end, said first arm segment connected end being joined to said connecting segment such that said first arm segment extends substantially perpendicularly and laterally from said connecting segment, and a cantilever second arm segment having a second arm segment free end and having a second arm segment connected end, said second arm segment connected end being joined to said connecting segment such that said first arm segment extends substantially perpendicularly and laterally from said connecting segment and spaced apart from said first arm segment, and such that an apparatus user can move into and out of said frame structure between said first and second arm segment free ends without crossing over any part of said frame structure.

4. The apparatus of claim 3, wherein said connecting segment is formed of two telescoping portions for convenient assembly and disassembly of said frame structure for transport and storage.

5. The apparatus of claim 3, wherein said winch support structure is located substantially at the middle of said connecting segment.

6. The apparatus of claim 3, wherein said winch support structure comprises a pair of spaced apart, substantially vertical members each removably joined to said connecting segment with disengagable mounting means including flexible and resilient plate members having stud ports and with studs protruding laterally from said vertical members and also from said connecting segment for fitting through said stud ports, wherein said plate members resiliently and removably retain said stud ports engagingly around said studs.

7. The apparatus of claim 6, wherein said vertical members are removably joined to said connecting segment with anchoring plates and fasteners passing through said anchoring plates into said vertical members and into said connecting segment.

8. The apparatus of claim 6, wherein said winch assembly comprises a spool rotatably mounted between said vertical members on an axle bolt, a worm wheel gear attached to said spool to rotate together with said spool and engaged by a worm gear rotatably mounted to said vertical member.

9. The apparatus of claim 3, additionally comprising a patient leg support box for supporting the lower legs of the patient to place the patient in a safe and effective traction receiving position.

10. The apparatus of claim 9, wherein said box comprises a top wall and a bottom wall and at least one side wall, and wherein said box additionally comprises a channel in said bottom wall for fitting over and around said second arm segment of said frame structure.

11. The apparatus of claim 10, wherein said box comprises leg retaining projections extending upward from said top wall.

12. The apparatus of claim 3, wherein said connecting segment is formed of a tubular center portion and two telescoping portions which fit into opposing ends of said center portion for convenient assembly and disassembly of said frame structure for transport and storage.

13. The apparatus of claim 3, additionally comprising a patient leg support stand for supporting the lower legs of the patient to place the patient in a safe and effective traction receiving position, comprising:

a top panel having opposing side edges and a front edge and a notch in said front edge sized to receive and retain the legs of the patient, an elongate top panel support member secured across said top panel and extending outward from said opposing side edges of said top panel and having a mounting opening at each end, two upright assemblies, each upright assembly having a series of mounting ports through one of which a fastener is inserted, said fastener also being inserted into one of said mounting openings.

14. The apparatus of claim 13, wherein said top panel has a bottom surface and wherein said support member is secured to said bottom surface of said top panel with strap elements fastened to said bottom surface.

15. The apparatus of claim 13, wherein said upright assemblies are each in the form of a substantially T-shaped panel having stand support leg portions protruding from the horizontal ends of the T-shape, and having a perpendicular slat protruding longitudinally from the vertical portion of the T-shape.

16. The apparatus of claim 15, wherein said upright assemblies each include first interconnecting slots on either side of the base of the T-shape to receive said cross braces.

17. The apparatus of claim 16, wherein said cross braces include second interconnecting slots which interlock with said first interconnecting slots.

18. The apparatus of claim 3, additionally comprising a cervical traction assembly secured to one said arm segment.

19. The apparatus of claim 18, wherein said cervical traction assembly comprises:

a head halter, a halter post secured to said one said arm segment, wherein one said cord extends around a first cervical pulley at the base of said halter post and around a second cervical pulley at the top of said halter post, and then is clipped to said halter.

20. A lumbar traction apparatus for applying traction to the back of a patient, comprising:

a frame structure including a connecting segment having two ends and arm segments, each segment attached to one of the ends of the connecting segment, a winch support structure extending above said frame structure and mounted centrally on the connecting segment, a winch assembly having hand crank means mounted on said winch support structure, two harnesses for wrapping around the torso of the patient, tensioning cords extending from said winch assembly each to one of said two harnesses, such that rotating said hand crank means on said winch assembly gathers both said cords and thereby pulls said harnesses apart to create traction in the back of the patient, wherein said winch support structure has a base, additionally comprising first guide pulleys attached to said connecting segment at said base of said winch support structure, second guide pulleys attached to the ends of said connecting segment, and third guide pulleys secured to said arm segments, wherein said tensioning cords extend from said winch assembly to said first guide pulleys, then said cords extend in opposite directions along said connecting segment to said second guide pulleys, and said cords extend from said second guide pulleys along said arm segments to said third guide pulleys, and each connect to one of said harnesses.

* * * * *